(12) United States Patent
Nakamura

(10) Patent No.: US 8,837,794 B2
(45) Date of Patent: Sep. 16, 2014

(54) MEDICAL IMAGE DISPLAY APPARATUS, MEDICAL IMAGE DISPLAY METHOD, AND MEDICAL IMAGE DISPLAY PROGRAM

(75) Inventor: Keigo Nakamura, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/499,202

(22) PCT Filed: Sep. 29, 2010

(86) PCT No.: PCT/JP2010/005870
§ 371 (c)(1),
(2), (4) Date: Mar. 29, 2012

(87) PCT Pub. No.: WO2011/040018
PCT Pub. Date: Apr. 7, 2011

(65) Prior Publication Data
US 2012/0183191 A1    Jul. 19, 2012

(30) Foreign Application Priority Data

Sep. 30, 2009  (JP) .................................. 2009-226065
Mar. 29, 2010  (JP) .................................. 2010-075500

(51) Int. Cl.
*G06K 9/00*    (2006.01)

(52) U.S. Cl.
USPC ....................................................... 382/128

(58) Field of Classification Search
USPC .......................... 382/128–134; 128/920–925;
356/39–49; 600/407–414, 424–426;
345/581–618; 250/455
See application file for complete search history.

(56) References Cited

U.S. PATENT DOCUMENTS

| 2002/0101436 | A1 | 8/2002 | Shastri et al. |
| 2002/0158875 | A1 | 10/2002 | Yamada |
| 2005/0226405 | A1 | 10/2005 | Fukatsu et al. |
| 2010/0080427 | A1* | 4/2010 | Yeluri et al. .................. 382/128 |

FOREIGN PATENT DOCUMENTS

| JP | H0449945 A | 2/1992 |
| JP | 2002-259006 A | 9/2002 |
| JP | 2002-324230 A | 11/2002 |
| JP | 2005-073818 A | 3/2005 |
| JP | 2005-301453 A | 10/2005 |

OTHER PUBLICATIONS

Chinese Office Action dated Nov. 8, 2013 issued in Chinese Patent Application No. 201080043879.8.
Japanese Office Action dated Sep. 10, 2013 issued in Japanese Patent Application No. 2010-075500.
Office Action, dated Mar. 4, 2014, issued by the Japanese Patent Office in corresponding Japanese Patent Application No. 2010-075500 and partial translation thereof.

* cited by examiner

*Primary Examiner* — Atiba O Fitzpatrick
(74) *Attorney, Agent, or Firm* — Sughrue Mion, PLLC

(57) ABSTRACT

A keyword extracting section extracts anatomical structures and/or information related to diseases from image observation reports regarding input image data. A display protocol determining section determines display protocols by selecting display protocols from among those stored in a display protocol table, based on the extracted anatomical structures and/or information related to diseases. Medical images for display are displayed based on the determined display protocols.

10 Claims, 21 Drawing Sheets

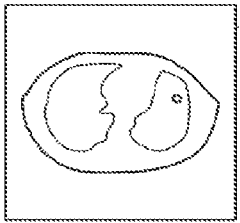

FIG.3B

IMAGE OBSERVATION REPORT

PATIENT ID : 12345   EXAMINATION ID : 1001
EXAMINATION DATE : 2009/9/18

OPINION

3cm DIAMETER NODULE PRESENT

IN UPPER LOBE S2 OF LEFT LUNG · · · · ·

ATTACHED IMAGES

| KEYWORDS | EXTRACTION TARGET TERMS |
|---|---|
| LUNG | LUNG/LUNG FIELD/RIGHT LUNG/LEFT LUNG/UPPER LOBE/MIDDLE LOBE/LOWER LOBE ... |
| LIVER | LIVER/RIGHT LOBE/LEFT LOBE/CAUDATE LOBE/DORSOLATERAL SEGMENT OF LEFT LOBE ... |
| HEART | HEART/RIGHT ATRIUM/RIGHT VENTRICLE/LEFT ATRIUM/LEFT VENTRICLE ... |
| BRAIN | HEAD/BRAIN/CEREBRUM/FRONTAL LOBE ... |
| BONE | BONE/RIB/VERTEBRA/PELVIS ... |
| BLOOD VESSEL | ARTERY/VEIN/PORTAL VEIN |
| INTERVERTEBRAL DISC | INTERVERTEBRAL DISC |
| NODULE | NODULE ... |
| TUMOR | TUMOR ... |
| GROUND GLASS OPACITY | GROUND GLASS OPACITY/GGO |
| STENOSIS | STENOSIS |
| OCCLUSION | OCCLUSION |
| HERNIA | HERNIA |
| CYST | CYST |
| BLEEDING | BLEEDING |
| CALCIFICATION | CALCIFICATION |
| CONSOLIDATION | CONSOLIDATION |
| Crazy-Paving | Crazy-Paving |
| HONEYCOMB SHADOW | HONEYCOMB SHADOW |
| EMPHYSEMA | EMPHYSEMA |
| DIFFUSE DISEASE | DIFFUSE DISEASE |

IMAGE OBSERVATION REPORT

PATIENT ID : 12345   EXAMINATION ID : 1081
EXAMINATION DATE : 2009/9/18

OPINION

2cm DIAMETER NODULE PRESENT
IN UPPER LOBE S2 OF LEFT LUNG

ATTACHED IMAGES

DETAILED OBSERVATION

K1 = LUNG, K2 = NODULE

| DISPLAY PROTOCOL ID | KEYWORD | REGION ID | POSITIONAL INFORMATION | IMAGE TO BE OBTAINED | IMAGE PROCESS 1 | IMAGE PROCESS 2 | ... |
|---|---|---|---|---|---|---|---|
| 001 | LUNG/NODULE | Sub1 | (0,0), W=512, H=512 | CT | AXIAL | LUNG FIELD CONDITIONS | |
| | | Sub2 | (0,512), W=512, H=512 | CT | CORONAL | LUNG FIELD CONDITIONS | |
| | | Sub3 | (512,0), W=512, H=512 | CT | AXIAL | MEDIASTINAL CONDITIONS | |
| | | Sub4 | (512,512), W=512, H=512 | CT | CORONAL | MEDIASTINAL CONDITIONS | |
| 002 | ... | ... | ... | ... | ... | ... | |

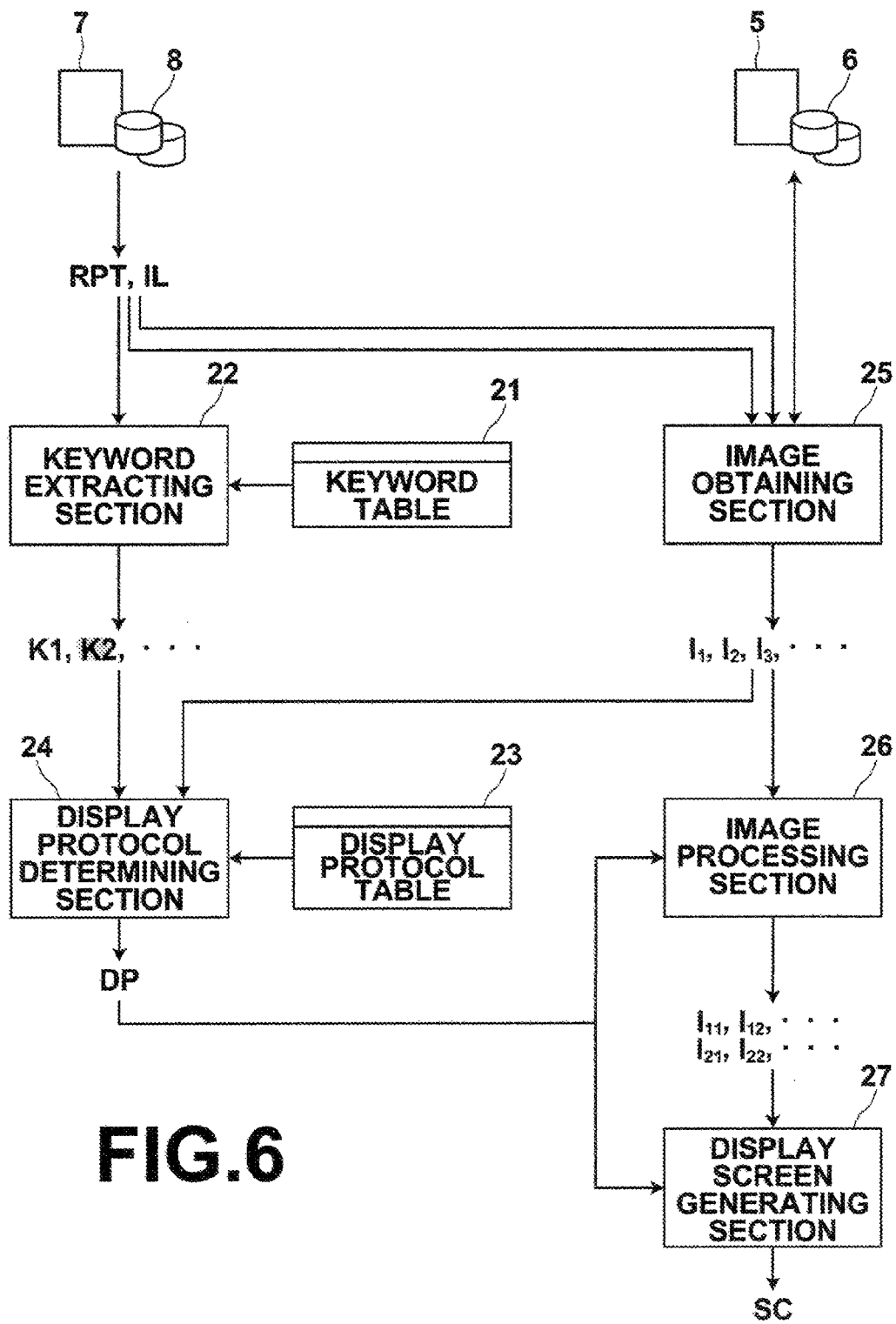

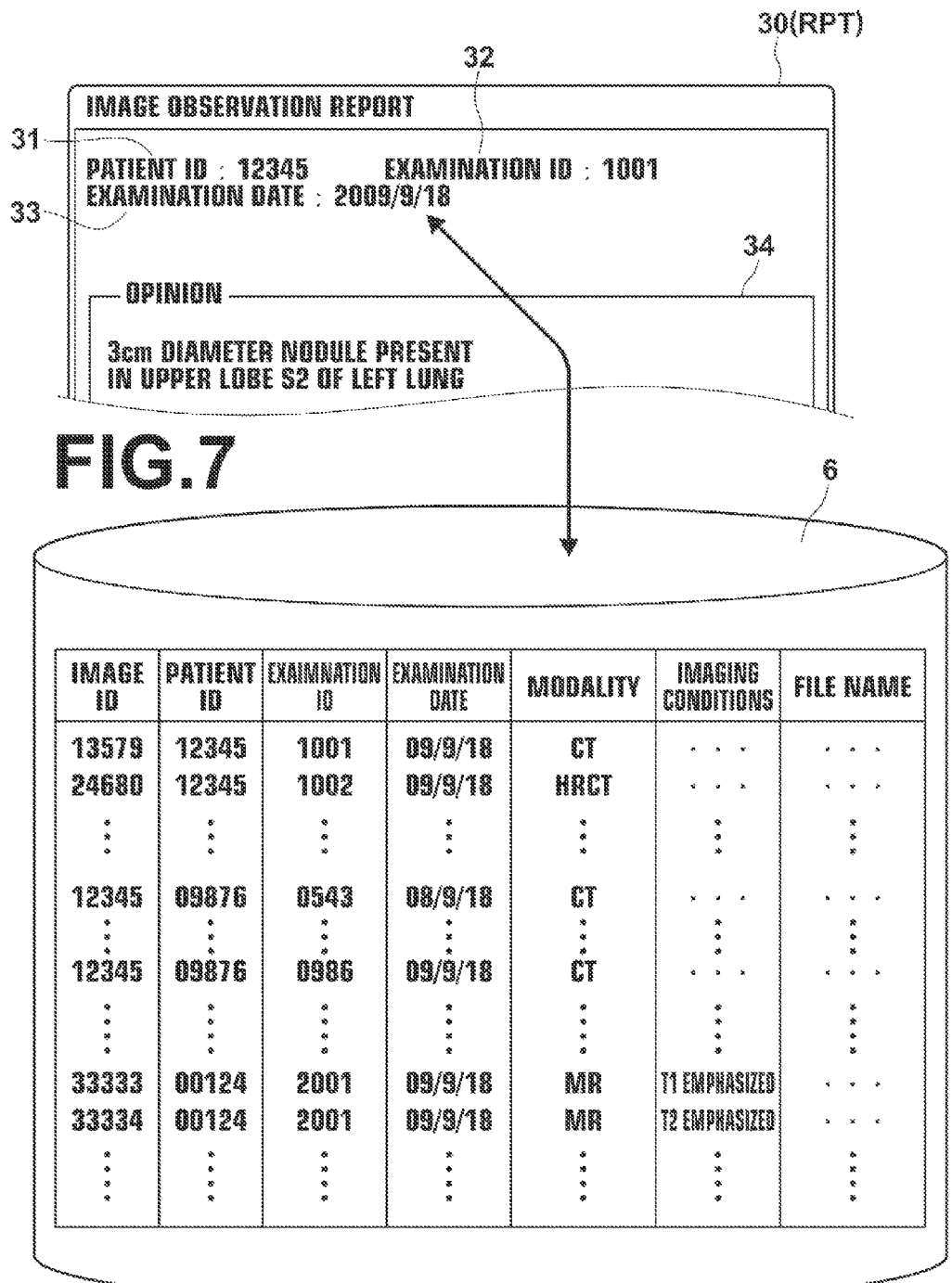

FIG.8A

| CT<br>AXIAL<br>LUNG FIELD<br>CONDITIONS | HRCT<br>AXIAL<br>LUNG FIELD<br>CONDITIONS |
|---|---|
| CT<br>AXIAL<br>MEDIASTINAL<br>CONDITIONS | HRCT<br>AXIAL<br>MEDIASTINAL<br>CONDITIONS |

LUNG NODULE

FIG. 8B

| DISPLAY PROTOCOL ID | KEYWORD | REGION ID | POSITIONAL INFORMATION | IMAGE TO BE OBTAINED | IMAGE PROCESS 1 | IMAGE PROCESS 2 | ... |
|---|---|---|---|---|---|---|---|
| 001 | LUNG/NODULE | Sub1 | (0,0), W=512, H=512 | INPUT CT | AXIAL | LUNG FIELD CONDITIONS | ... |
| | | Sub2 | (0,512), W=512, H=512 | INPUT CT | CORONAL | LUNG FIELD CONDITIONS | ... |
| | | Sub3 | (512,0), W=512, H=512 | SAME DAY HRCT | AXIAL | MEDIASTINAL CONDITIONS | ... |
| | | Sub4 | (512,512), W=512, H=512 | SAME DAY HRCT | CORONAL | MEDIASTINAL CONDITIONS | ... |
| | ... | ... | ... | ... | ... | ... | |
| 002 | ... | | | | | | |

FIG.9A

| CT AXIAL LUNG FIELD CONDITIONS | CT SCOUT IMAGE |
|---|---|
| CT AXIAL MEDIASTINAL CONDITIONS | HRCT AXIAL MEDIASTINAL CONDITIONS |

DIFFUSE LUNG DISEASE

FIG.9B

| CT AXIAL LUNG FIELD CONDITIONS | CR |
|---|---|
| CT AXIAL MEDIASTINAL CONDITIONS | |

LUNG NODULE
(CR AND CT)

FIG.9C

| PRESENT CT AXIAL LUNG FIELD CONDITIONS | PAST CT AXIAL LUNG FIELD CONDITIONS | PRESENT HRCT AXIAL SINGLE LUNG FIELD CONDITIONS | PAST HRCT AXIAL SINGLE LUNG FIELD CONDITIONS |
|---|---|---|---|
| PRESENT CT AXIAL MEDIASTINAL CONDITIONS | PAST CT AXIAL MEDIASTINAL CONDITIONS | PRESENT HRCT AXIAL SINGLE LUNG MEDIASTINAL CONDITIONS | PAST HRCT AXIAL SINGLE LUNG MEDIASTINAL CONDITIONS |

LUNG NODULE
(PRESENT AND PAST CR AND CT)

FIG.9D

| MR T2 EMPHASIZED IMAGE | MR T1 EMPHASIZED IMAGE | MRA MIP |
|---|---|---|
| MR FLAIR | MR DWI | |

CEREBRAL ALZHEIMER'S

INTERVERTEBRAL HERNIA

FIG.11A

| CT AXIAL ARTERIAL PHASE | CT AXIAL PORTAL VEIN PHASE |
|---|---|
| CT AXIAL DELAYED PHASE | NONE |

LIVER TUMOR

FIG.11B

| CT AXIAL ARTERIAL PHASE | CT AXIAL PORTAL VEIN PHASE |
|---|---|
| CT AXIAL DELAYED PHASE | VR IMAGE OF CT AXIAL ARTERIAL PHASE |

LIVER TUMOR

FIG. 13

| DISPLAY PROTOCOL ID (IMAGE PROCESSING CONDITION ID) | KEYWORD | IMAGE TYPE | MASK 1 (AUTOMATIC DETECTION TARGET) | DISPLAY/ NON DISPLAY | MASK 2 (AUTOMATIC DETECTION TARGET) | DISPLAY/ NON DISPLAY | COLOR TEMPLATE |
|---|---|---|---|---|---|---|---|
| 101 | LIVER | VR | LIVER | DISPLAY | | | COLOR 01 |
| 102 | LIVER/SPLEEN | VR | LIVER | DISPLAY | SPLEEN | DISPLAY | COLOR 02 |
| 103 | BLOOD VESSEL | VR | BONE | NON DISPLAY | | | COLOR 11 |
| 104 | HEART | VR | HEART | DISPLAY | CORONARY ARTERY | DISPLAY | COLOR 21 |
| 105 | BRAIN/BLOOD VESSEL | MIP | | | | | MONOCHROME 01 |
| 106 | BRAIN/BLOOD VESSEL | VR | BLOOD VESSEL | DISPLAY | | | COLOR 31 |

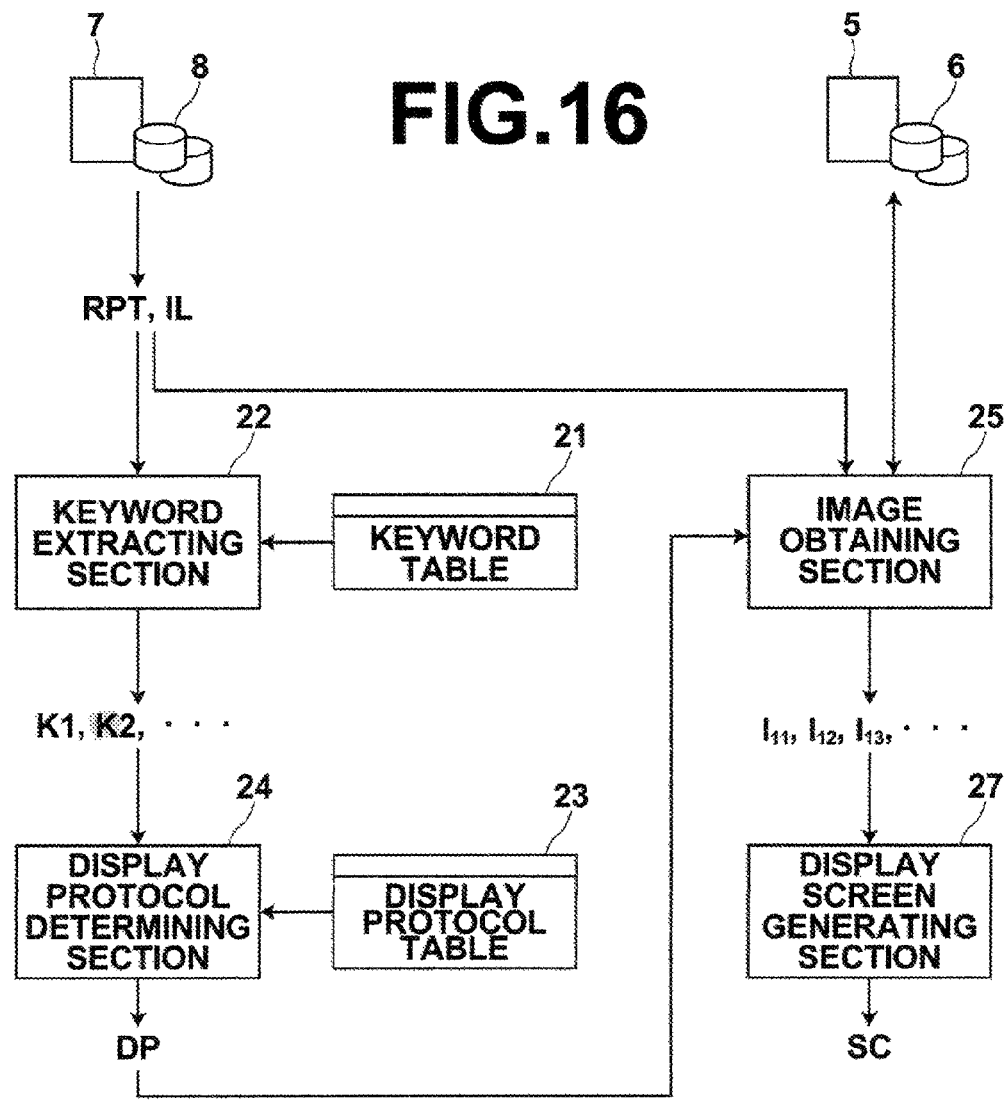

MEDICAL IMAGE DISPLAY APPARATUS, MEDICAL IMAGE DISPLAY METHOD, AND MEDICAL IMAGE DISPLAY PROGRAM

CROSS REFERENCE TO RELATED APPLICATION

This application is a National Stage of International Application No. PCT/JP2010/005870, filed on Sep. 29, 2010, claiming priority based on Japanese Patent Application Nos. 2009-226065, filed on Sep. 30, 2009 and 2010-075500, filed Mar. 29, 2010, the contents of all of which are incorporated herein by reference in their entirety.

TECHNICAL FIELD

The present invention is related to a medical image display apparatus, and a medical image display method that determine display formats of medical images by utilizing image observation report information. The present invention is also related to a medical image display program that causes a computer to execute the medical image display method.

BACKGROUND ART

Recently, image diagnosis using medical images that represent the interiors of living subjects is becoming widely used. Various modalities, such as X ray imaging apparatuses that employ FPD's (flat panel X ray detectors), X ray CT apparatuses, US (Ultra Sound) diagnosis apparatuses, MRI apparatuses, and PET apparatuses are utilized to obtain the medical images.

In actual image diagnosis settings, it is often the case that diagnosis is performed by cooperation between physicians of various specialties who request image diagnosis (hereinafter, requesting physicians) and physicians whose specialty is observing medical images (hereinafter, radiologists). Specifically, radiation technicians perform imaging of patients to obtain medical images based on examination orders from requesting physicians. Then, radiologists observe the medical images, generate reports that summarize the image observation results, and provide the reports to the requesting physicians. The requesting physicians ultimately perform diagnoses by reading the opinions written in the generated reports, referring to the images included in the reports, and taking various other pieces of information, such as the results of patient interviews and the results of other tests, into consideration.

A medical report generation/referral apparatus that generates and enables referral to medical reports is known (Patent Document 1). In this apparatus, links that correlate the addresses and image editing parameters, such as window levels, window widths, and magnification rates, of medical images to be referred to with keyword text included in opinions are generated according to user input. This is to clarify the relationships between portions of the contents of the opinions and each of a plurality of images included in the reports. Further, when viewers click on the text while referring to the reports, the linked medical images are edited based on the image editing parameters and displayed.

Meanwhile, a medical image display apparatus that realizes image display according to the needs of image observers is known (Patent Document 2). In this apparatus, image observation modes (a single image observation mode and a comparative image observation mode, for example) that define a display position and an image layout (number of screen divisions, tile display/stacked display, whether scout images are displayed, whether lines that indicate slice positions are displayed) for each modality of images to be displayed are set in advance. During image observation, the images to be displayed are displayed based on the image observation mode selected by the image observer.

In addition, an apparatus that automatically generates display protocol sequences is known (Patent Document 3). This apparatus switches a plurality of display protocols, in which a plurality of image display conditions (such as layouts and order of display) and image processing conditions are defined, in a predetermined order based on at least one display protocol sequence, to cause a display means to display a plurality of images while switching the display conditions and image processing conditions therefor. This apparatus automatically generates display protocol sequences according to examinations, series, the types of images, the types of input modalities, the physician who is to observe the images or the group that the physician belongs to (radiologist, clinical physician, a referring physician, etc.), and the intended uses of the images (observation, referral, comparison, etc.).

PRIOR ART DOCUMENTS

[Patent Document 1]
 Japanese Unexamined Patent Publication No. 2005-301453
[Patent Document 2]
 Japanese Unexamined Patent Publication No. 2005-073818
[Patent Document 3]
 Japanese Unexamined Patent Publication No. 2002-259006

In the image diagnosis workflow including cooperation between radiologists and requesting physicians described above, the objectives of image observation differ between the radiologists and the requesting physicians. That is, the objective of radiologists is to detect or discriminate diseases by observing the medical images. On the other hand, the objective of requesting physicians is to observe the detected diseases in detail, to generate surgical plans, and to explain the diseases to patients.

The apparatus disclosed in Patent Document 1 displays images to be referred to as set by a radiologist when the radiologist generates the image observation report. In view of the differences in objectives of image observation, however, when a requesting physician refers to the image observation report, it is not sufficient to merely confirm the images included in the image observation report, and there may be cases in which the requesting physician wishes to observe other images for more detailed observation. Such possible cases are those in which the requesting physician wishes to observe images of cross sections adjacent to an included axial tomographic image, MPR images imaged at cross sections having different angles, etc.

In addition, cases may be considered in which radiologists and requesting physicians wish for display of medical images in different formats. A specific example of such a case is that in which a radiologist generates an image observation report including axial tomographic images employed for image observation, whereas a requesting physician may wish to observe volume rendered images, to which the requesting physician is more familiar with due to their use in surgical simulations and the like.

In cases in which requesting physicians wish to observe medical images in formats different from those of images included in image observation reports, it is necessary for radiologists to generate images as desired by the requesting physicians and to generate image observation reports such that images are displayed in the display formats desired by the requesting physicians. Alternatively, it is necessary for the requesting physicians to operate image display apparatuses themselves to generate desired images and to set image display layouts. That is, there is room for improvement from the viewpoints of work burden and efficiency.

In addition, there are requesting physicians who believe that observation is facilitated if the types of images and the display formats of images are changed according to the type of disease or the anatomical structure (organ) in which diseases are present. For example, lung nodules and diffuse lung disease are both diseases of the lung. However, there are requesting physicians that prefer observation of the lung as axial tomographic images in the case that the disease is lung nodules, and prefer observation of the lung as coronal tomographic images in the case that the disease is a diffuse lung disease. In addition, there are requesting physicians that prefer observation of liver tumors in volume rendered images, and prefer observation of lung tumors in axial tomographic images.

In this respect, it is necessary for the apparatus disclosed in Patent Document 1 to set links between text and the addresses and image editing parameters of medical images for each image observation report. For example, in the case that there are a plurality of image observation reports in which the same disease is found, it becomes necessary to set links to image editing parameters for the same text in each of the reports individually, and there is room for improvement from the viewpoint of efficiency in generating image observation reports.

It is not necessary for the apparatus disclosed in Patent Document 2 to perform detailed setting operations of image observation modes each time that images are observed, by setting image observation modes according to the needs of requesting physicians in advance. However, if image observation modes are set not only according to the modalities of images to be displayed but also according to other factors such as types of disease and anatomical structures, the number of image observation modes will become great. In such a case, it becomes necessary for the requesting physicians to memorize combinations between each of the set image observation modes and display formats in order for images to be displayed in appropriate image observation modes. This places a great burden on the requesting physicians.

Further, the apparatus disclosed in Patent Document 3 automatically generates display protocol sequences according to examinations, series, the types of images, the types of input modalities, the physician who is to observe the images, the location at which the images are utilized, and the intended uses of the images. However, Patent Document 3 neither discloses nor suggests how parameters are obtained. In the case that parameters are set manually each time that the images are displayed, such operations are troublesome.

Further, the above patent documents are silent regarding changing the display format of medical images according to the type of disease or the anatomical structure (organ) in which the disease is present.

The present invention has been developed in view of the foregoing circumstances. It is an object of the present invention to provide a medical image display apparatus, a medical image display method, and a medical image display program that streamline image diagnosis workflow including cooperation between radiologists and requesting physicians and enables display of medical images in display formats desired by requesting physicians, without burdening the radiologists or the requesting physicians with extraneous workloads.

DISCLOSURE OF THE INVENTION

A medical image display apparatus of the present invention is characterized by comprising:

display protocol storing means, for storing display protocols, which are defined by image processing conditions for generating medical images for display from input medical image data and/or display conditions of the medical images for display being correlated with information regarding anatomical structures and/or information regarding diseases;

extracting means, for extracting information regarding anatomical structures and/or information regarding diseases from within medical opinions regarding observation target images included in image observation report information regarding the input medical image data;

display protocol determining means, for determining display protocols for the medical images for display by selecting display protocols from among those stored in the display protocol storing means, based on the extracted information regarding anatomical structures and/or information regarding diseases; and image processing/display control means, for generating the medical images for display from the input medical image data and/or controlling display of the medical images for display, based on the determined display protocols.

A medical image display method of the present invention is characterized by comprising the steps of:

extracting information regarding anatomical structures and/or information regarding diseases from within medical opinions regarding observation target images included in image observation report information regarding input medical image data;

determining display protocols for the medical images for display by selecting display protocols from among display protocols, which are defined by image processing conditions for generating medical images for display from input medical image data and/or display conditions of the medical images for display being correlated with information regarding anatomical structures and/or information regarding diseases, based on the extracted information regarding anatomical structures and/or information regarding diseases; and generating the medical images for display from the input medical image data and/or controlling display of the medical images for display, based on the determined display protocols.

A medical image display program of the present invention is that which causes a computer to execute the above method.

In the present invention, the image processing conditions include: conditions that represent the types of images to be generated, such as MPR, MIP, MinIP, and volume rendered images; detailed image processing parameters, such as the position and inclination of cross sections, the positions of viewpoints, the directions of line of sight vectors, and degrees of opacity; and various other conditions such as window widths, window levels, and CAD (Computer Aided Diagnosis) processing.

The display conditions include various conditions, such as: numbers of images to be displayed within a single screen; the sizes of each displayed image; layouts; and orders of display.

The anatomical structures which are correlated with the image processing conditions and display conditions may include those having various viewpoints and units, such as imaged portions, organs, and tissue. Specific examples include: imaged portions such as the head and the chest; organs such as the brain, the lung, and the liver; portions of organs such as the frontal lobe, the left lung, the left upper love of the lung, and lung sections; tissue such as bones and blood vessels; and specific bones and blood vessels such as the fifth lumbar vertebrae and the coronary artery.

Information related to diseases is information related to diseases within the aforementioned anatomical structures. Specific examples include: nodules, tumors, stenosis, and occlusions.

Accordingly, the display protocols of the present invention are those in which image processing conditions and display conditions suited for observation of images are defined for each of the above anatomical structures and diseases.

Extraction of the anatomical structures and/or the information related to diseases from the image observation report information may be performed by preparing keywords that represent anatomical structures and/or information related to diseases in advance, and extracting these keywords from the image observation report information. Alternatively, other known language analysis techniques may be employed.

The display protocols may be determined by storing a plurality of predefined display protocols for each anatomical structure and/or each piece of information related to disease, and selecting display protocols associated with the anatomical structures and/or the information related to diseases extracted from the image observation report information. In this case, it is preferable for a configuration to be adopted in which the stored display protocols can be changed and/or new display protocols can be added. Alternatively, display protocols may be generated based on the anatomical structures and/or the information related to diseases extracted from the image observation report information by employing a known technique, such as machine learning.

The display protocols may be further correlated with the modalities of the input medical image data, and define image processing conditions and display conditions for each of the anatomical structures and diseases for each modality. In this case, the display protocol for the input medical image data is determined not only based on the anatomical structures and/or the information related to diseases, but further on the modality of the input medical image data.

In addition, user information that identifies users of the medical image display apparatus may be obtained, the display protocols may be correlated with user information or group information that identifies groups constituted by a plurality of users, and the display protocol determining means may determine the display protocol based further on the user information or the group information.

It is preferable for the images for display in the present invention to be not only those generated from the input medical image data which were the subjects of the image observation reports, but also images generated from relevant medical image data, which have a predetermined relevancy to the input medical image data.

Here, specific examples of the predetermined relevancy include: image data of the same patient as that of the input medical image data; image data obtained by the same modality as that of the input medical image data; image data obtained by a different modality from that of the input image data; and image data that represents the same anatomical structure and/or the same disease as that of the input medical image data.

In this case, the display protocol may further define image processing conditions for generating relevant medical images for display from relevant medical image data, which have the predetermined relevancy to the input medical image data, and display conditions for the relevant medical images for display.

The relevant medical image data may be obtained by searching in a medical image database, in which medical image data and attribute information regarding the medical image data to be utilized when judging whether the predetermined relevancy exists, are stored. Information appended to the input medical image data or information obtained from the image observation report information regarding the input medical image data to be utilized to judge whether the predetermined relevancy exists may be used as search keys in such searches.

The relevant medical image data from which the relevant medical images for display are to be generated may be determined based on the results of the searches as well as the display protocols when the display protocols are determined. Then, the relevant medical image data from which the relevant medical images for display are to be generated may be obtained from the medical image database, and the medical images for display and the relevant medical images for display may be displayed, based on the determined display protocols.

Alternatively, the aforementioned searches may not be performed, and the display protocols may be determined not based on the results of the searches. Then, the relevant medical image data having the predetermined relevancy to the input medical images defined in the display protocol may be obtained from the medical image database, and the medical images for display and the relevant medical images for display may be displayed, based on the determined display protocols.

According to the present invention, information regarding anatomical structures and/or information regarding diseases is extracted from image observation report information regarding input medical image data. Display protocols are determined with respect to the input medical image data by selection from among stored display protocols based on the extracted information regarding anatomical structures and/or the extracted information regarding diseases. Medical images for display are enabled to be displayed based on the determined display protocols. Thereby, requesting physicians are enabled to observe images displayed based on display protocols which are automatically determined from image observation reports generated by radiologists. Accordingly, the requesting physicians can perform detailed observation of images in display formats suited to image observation results while effectively utilizing the image observation results provided by the radiologists without burdening either with extraneous workloads. The present invention streamlines the workflow of image diagnosis that includes cooperation between radiologists and requesting physicians in this manner.

In addition, the display protocols are automatically determined based on anatomical structures and diseases which are mentioned in the image observation reports. Therefore, the requesting physicians can perform detailed observation of images in display formats which are optimal for the diseases detected by the radiologists.

The display protocols may be determined based further on the modality of the input medical image data. In this case, observation of images in display formats optimal for the modality of the input medical image data becomes possible, which contributes to improvements in the efficiency and accuracy of diagnoses.

The display protocols may further define relevant medical image data having the predetermined relevancy to the input medical data, and the relevant medical image data may be searched for within the medical image database and displayed. In this case, comparative observation with optimal relevant medical images according to anatomical structures or diseases becomes possible, which contributes to improvements in the efficiency and accuracy of diagnoses.

The display protocols may be defined for each user or each group of users, user information that identifies users may be obtained, and the display protocols may be determined according to the obtained user information. In this case, the same anatomical structures or diseases may be displayed as medical images based on different display protocols for each physician or for each group of physicians, such as a practice group. Thereby, display of images more finely attuned according to individual preferences can be realized.

BRIEF DESCRIPTION OF THE DRAWINGS

FIG. 3A is a diagram that schematically illustrates an example of an image observation report display screen.

FIG. 3B is a diagram that schematically illustrates another example of an image observation report display screen.

FIG. 4 is a diagram that schematically illustrates a process for extracting keywords from an opinion in an image observation report and from a keyword table.

FIG. 5B is a diagram that illustrates an example of a display protocol table.

FIG. 6 is a block diagram that schematically illustrates the structures and the flow of processes that realize the medical image display function of a second embodiment of the present invention.

FIG. 7 is a diagram that schematically illustrates a process for obtaining relevant images from information in an image observation report and information in an image information database.

FIG. 8A is a diagram that illustrates an example of a display protocol that simultaneously displays an image which is a target of image observation and a relevant image.

FIG. 8B is a diagram that illustrates an example of a display protocol table that includes the display protocol of FIG. 8A.

FIG. 9A is a first diagram that schematically illustrates another example of a display protocol that simultaneously displays an image which is a target of image observation and a relevant image.

FIG. 9B is a second diagram that schematically illustrates another example of a display protocol that simultaneously displays an image which is a target of image observation and a relevant image.

FIG. 9C is a third diagram that schematically illustrates another example of a display protocol that simultaneously displays an image which is a target of image observation and a relevant image.

FIG. 9D is a fourth diagram that schematically illustrates another example of a display protocol that simultaneously displays an image which is a target of image observation and a relevant image.

FIG. 11A is a diagram that illustrates an example of different display protocols for the same organ and the same disease.

FIG. 11B is a diagram that illustrates another example of different display protocols for the same organ and the same disease.

FIG. 13 is a diagram that illustrates a display protocol table that only defines image processing conditions.

FIG. 16 is a block diagram that schematically illustrates the structures and the flow of processes that realize the medical image display function of a fourth embodiment of the present invention.

BEST MODE FOR CARRYING OUT THE INVENTION

Hereinafter, embodiments of the present invention will be described with reference to the attached drawings.

Figure 1:
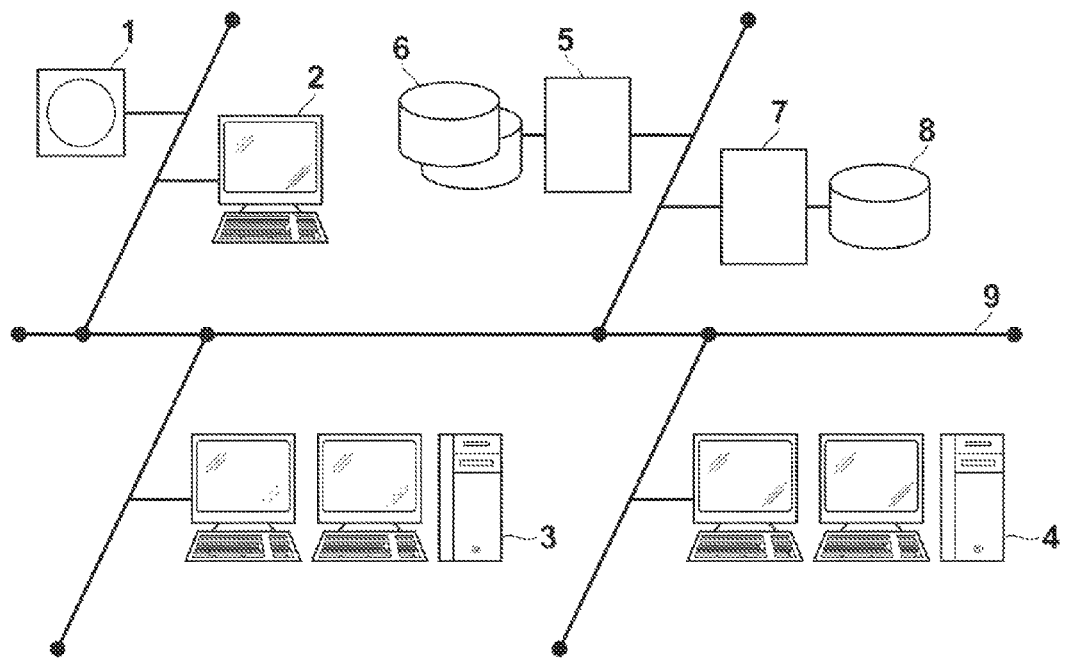
FIG. 1 is a diagram that schematically illustrates the configuration of a medical information system in which a medical image display apparatus according to a first embodiment of the present invention is incorporated.

FIG. 1 is a diagram that illustrates the schematic configuration of a medical information system in which a medical image display apparatus according to a first embodiment of the present invention is incorporated. The system obtains and stores images of examination target portions of subjects based on examination orders by physicians in practice groups employing a known ordering system, enables observation of the obtained images and generation of image observation reports by radiologists, and enables viewing of the image observation reports and detailed observation of the images which were the targets of image observation by the physicians in the practice group who requested image diagnosis. As illustrated in FIG. 1, the system is equipped with: an imaging modality 1 for obtaining medical images; an image quality assurance checking work station (QA-WS) 2; a radiology work station 3; a practice group work station 4; an image information managing server 5; an image information database 6; an image observation report managing server 7; and an image observation report database 8. Each component is connected to each other so as to be capable of communications via a network 9. The components are controlled by programs installed from recording media, such as CD-ROM's. The programs may alternatively be downloaded via a network, such as the Internet, from a server, and then installed.

The imaging modality 1 includes an apparatus that generates three dimensional image data that represent three dimensional images of examination target portions of subjects by imaging these portions, attaches data defined by DICOM standards to the image data, and outputs the image data. Specific examples of the imaging modality 1 include: a CT (Computed Tomography) apparatus; an MR (Magnetic Resonance) apparatus; an X ray imaging apparatus; a PET (Positron Emission Tomography) apparatus, an ultrasound imaging apparatus, and X ray imaging apparatus that employ FPD's (Flat Panel X ray Detectors). Note that hereinafter, combinations of the image data that represent subjects and the data attached to the image data will be referred to as "image information". That is, the "image information" includes text data related to images.

The QA-WS 2 is constituted by a general use processing apparatus (computer), one or two high resolution displays, and input devices such as a keyboard and a mouse. Software that assists the work of examining technicians is incorporated into the processing apparatus. The QA-WS 2 receives image information according to the DICOM standard from the modality 1 by functions realized by executing the software program. Then, the image data included in the received image information and the contents of the attached data are displayed on a screen, to solicit the examination technician for confirmation. Image information which has been confirmed by the examination technician is transferred to the image information managing server 5 via the network 9, and a request to register the image information in the image information database 6 is sent.

The radiology work station 3 is utilized by radiologists to observe images and to generate image observation reports. The radiology work station 3 is equipped with known hardware components, such as a CPU, a main memory device, an auxiliary memory device, input/output interfaces, a communications interface, input devices, a display device, and a data bus. A known operating system is installed in the radiology work station 3. The radiology work station 3 is equipped with one or two high fidelity displays as the display device. The radiology work station 3 performs processes such as requesting the image information managing server 5 to view images, displaying images received from the image information managing server 5, automatic detection/emphasized display of portions of images which appear to be diseased, assisting generation of image observation reports, requesting the image observation report server 7 to register and to view image observation reports, and displaying image observation reports received from the image observation report server 7. These processes are performed by software for each process being executed.

The practice group workstation 4 is utilized by physicians in practice groups to view detailed images and image observation reports, and to view/input electronic charts. The practice group work station 4 is equipped with known hardware components, such as a CPU, a main memory device, an auxiliary memory device, input/output interfaces, a communications interface, input devices, a display device, and a data bus. A known operating system is installed in the practice group work station 4. The practice group work station 4 is equipped with one or two high fidelity displays as the display device. The practice group work station 4 performs processes such as requesting the image information managing server 5 to view images, displaying images received from the image information managing server 5, automatic detection/emphasized display of portions of images which appear to be diseased, requesting the image observation report server 7 to view image observation reports, and displaying image observation reports received from the image observation report server 7. These processes are performed by software for each process being executed. The medical image display apparatus of the present invention is incorporated into the practice group work station 4. This will be described later.

The image information managing server 5 is a comparatively high performance general use computer which has built in software that provides the functions of a DBMS (DataBase Management System). The image information managing server 5 is equipped with a high capacity storage that constitutes the image information database 6. In the present specification, the storage that constitutes each database may be a high capacity hard disk device connected to the managing server corresponding thereto by a data bus. Alternatively, the storage may be an NAS (Network Attached Storage) or an SAN (Storage Area Network) which is connected to the network 9.

The image information database 6 has image data that represent images of subjects and additional data attached thereto registered therein. The attached additional data may include: image ID's for identifying individual images; patient ID's for identifying subjects; examination ID's for identifying examinations; unique ID's (UID's) which are assigned to each piece of image information; the time/date of examination when the image information was generated; the type of modality utilized during examinations to obtain image information; patient information such as the name, age, and sex of the patient; examined portions (imaged portions); imaging conditions (whether an imaging agent was utilized/utilized pigment, radiation nuclide, radiation dosage, etc.); and series numbers or collection numbers in the case that a plurality of images are obtained during a single examination. The image data are managed as XML or SGML data files.

When the image information managing server 5 receives requests to register image information from the QA-WS 2, the image information is organized into a format for the database and registered in the image information database 6.

In addition, when viewing requests are received from the radiology work station 3 or the practice group work station 4, the image information managing server 5 searches for the image information from among image information registered in the image information database 6, and transmits extracted image information to the radiology work station 3 or the practice group work station 4 that sent the request.

When a radiologist or a physician in a practice group performs operations to request viewing of an image for observation, the radiology work station 3 or the practice group work station 4 transmits a viewing request to the image information managing server 5, and obtains the image information necessary for observation. Then, the image information is displayed on the screen of a monitor, and executes automatic disease detection processes and the like according to input user requests.

The radiology work station 3 displays a report generating screen that assists generation of image observation reports on the monitor. When the radiologist inputs text that represents the contents of medical opinions performed based on image observation, the radiology work station 3 generates an image observation report, in which the input information and the image which was the target of observation (hereinafter, observation target image) is recorded. The radiology work station 3 transmits the generated image observation report to the image observation report managing server 7 via the network 9, and sends a request to register the image observation report in the image observation report database 8.

The image observation report managing server 7 is a comparatively high performance general use computer which has built in software that provides the functions of a DBMS (DataBase Management System). When the image observation report managing server 7 receives requests to register image observation reports from the image diagnosis medical work stations 3, the image observation reports are organized into a format for the database and registered in the image observation report database 8.

The image observation report database 8 has registered therein image ID's for identifying observation target images or representative images, observer ID's for identifying radiologists who performed image observation, positional information related to regions of interest, medical opinions, and the degrees of certainty of the medical opinions, for example. In addition, examination ID's and patient ID's, obtained by referring to the additional data attached to the image information, and further, image data that represent the observation target images or the representative images themselves may also be registered in the image observation report database 8. The image data may be copies of the image data which are registered in the image information database 6. Alternatively, the image data may be reduced image data, which have fewer numbers of pixels (thinned out) than the image data registered in the image information database 6. As a further alternative, the image data may be link data that indicate the storage locations of the image data within the image information database 6 and the file names thereof. In addition, the positional information related to regions of interest may be registered in the image information database 6 as part of the additional data attached to the image data, instead of in the image observation report database 8. Note that the image observation reports are managed as XML or SGML data files.

When viewing requests are received from the radiology work station 3 or the practice group work station 4, the image observation report managing server 7 searches for the image observation reports from among image observation reports registered in the image observation report database 8, and transmits extracted image observation reports to the radiology work station 3 or the practice group work station 4 that sent the request.

The network 9 is a local area network that connects various apparatuses within a hospital. However, in the case that the image diagnosis medical work stations 3 are provided at a different hospital or clinic, the network 9 may be local area networks of hospitals which are connected to each other via the Internet or via dedicated lines. In both cases, it is desirable for the network 9 to be that which enables high speed transfer of image information, such as an optical network.

Figure 2:
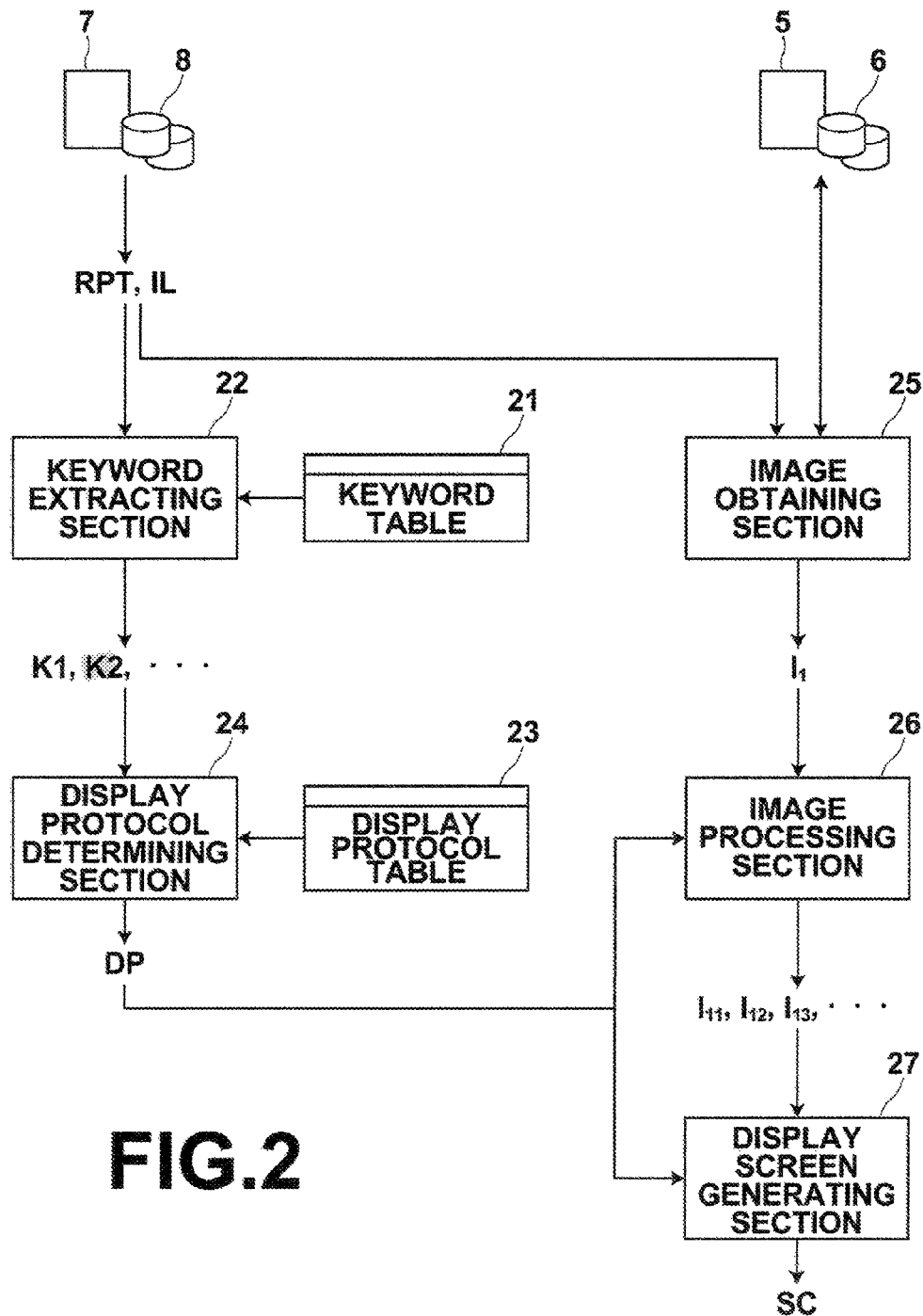
FIG. 2 is a block diagram that schematically illustrates the structures and the flow of processes that realize the medical image display function of the first embodiment of the present invention.

FIG. 2 is a block diagram that schematically illustrates the structures and the flow of data of a medical image display apparatus according to the first embodiment of the present invention that enables a cooperative viewing function of image observation reports and images which are the subjects of the image observation reports at the practice group work station 4. As illustrated in FIG. 2, the medical image display apparatus of the present invention is constituted by: a keyword table 21, a keyword extracting section 22, a display protocol table 23, a display protocol determining section 24, an image obtaining section 25, an image processing section 26, and a display screen generating section 27.

First, a software program that realizes the cooperative viewing function is booted up by performing an operation to observe an image, which is the subject of an image observation report, in detail while viewing the image observation report. FIG. 3A and FIG. 3B are diagrams that illustrate specific examples of cases in which the boot up operation is performed in a display screen of an image observation report. As illustrated in FIG. 3A, a display screen 30 of the image observation report is constituted by a region 31 in which a patient ID is displayed, a region 32 in which an examination ID is displayed, a region 33 in which an examination date is displayed, a region 34 in which medical opinions regarding an observation target image is displayed, a region 35 in which a thumbnail image 36 of the observation target image or a representative image is displayed, and a detailed observation button 37. The software program is booted up when a physician in a practice group, who is a user, depresses the detailed observation button 37 by clicking a mouse of the practice group workstation 4. FIG. 3B illustrates an example in which the detailed observation button 37 is not displayed. In this example, the software program is booted up by double clicking the image 36, for which detailed observation is desired.

When the software program is booted up, the keyword extracting section 22 analyzes opinion information (the contents displayed in the opinion regions of FIG. 3A and FIG. 3B) of the image observation report RPT using the keyword table 21, and extracts keywords K1 and K2, which are factors for determining a display protocol. FIG. 4 is a diagram that schematically illustrates an example of the specific contents of this process. As illustrated in FIG. 4, the keyword table 21 is a table in which keywords and extraction target terms are correlated. Information related to anatomical structures and information related to diseases are registered in the keyword table 21 as keywords and as extraction target terms. The keyword extracting section 22 searches the opinion information of the image observation report RPT to judge whether extraction target terms registered in the keyword table 21 are present therein. In this example, the terms "left lung", "upper lobe", and "nodule" within the medical opinion match extraction target terms. Next, the keyword extracting section 22 converts the extraction target terms that were found in the search into keywords. That is, the terms "left lung" and "upper lobe" are converted to a keyword "lung" (keyword K1) which is correlated thereto, and the term "nodule" is converted to a keyword "nodule" (keyword K2).

Here, the method for extracting keywords is not limited to that described above. Known natural language processing techniques which are employed by search engines, etc., may be applied, for example. However, by standardizing the names of anatomical structures and diseases by providing a user interface that enables selective input of anatomical structures and diseases when generating image observation reports, sufficient results can be obtained by searches that employ the keyword table described above.

In addition, in the case that links that correlate keywords in opinions and images to be referred to associated with the keywords are generated as in the apparatus disclosed in Patent Document 1 in the example illustrated in FIG. 3B, that is, if the "upper lobe S2 of left lung" and "nodule" in the opinion of FIG. 3B are correlated with the attached image 36, for example, the keyword extracting section 22 can follow the links when the software program is booted up by the attached image 36 being double clicked to extract the "upper lobe S2 of left lung" and "nodule" correlated with the specified attached image 36, then convert these terms to the keywords "lung" and "nodule" using the keyword table 21.

Note that maintenance such as registration, changes, and deletion of keywords in the keyword table 21 is possible through a predetermined GUI according to the needs of practice group physicians as necessary.

Next, the display protocol determining section 24 refers to the display protocol table 23 using the keywords K1 and K2 extracted by the keyword extracting section 22, and specifies a display protocol correlated to the keywords K1 and K2.

Figure 5A:
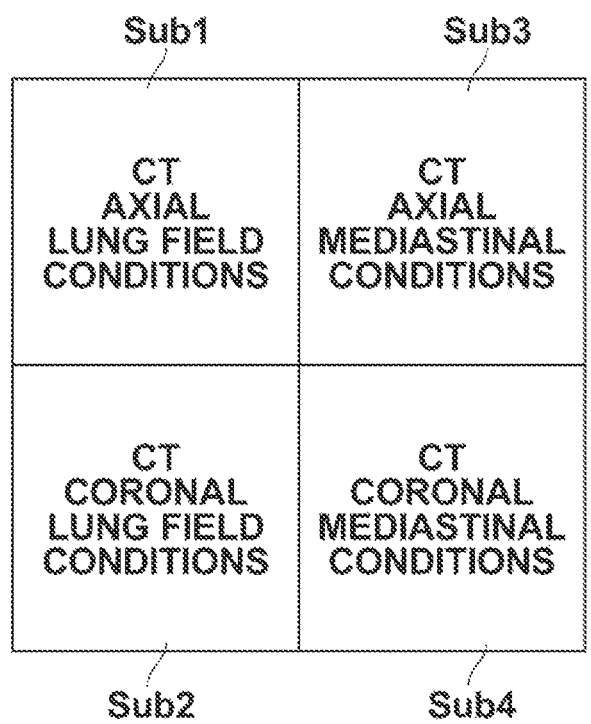
FIG. 5A is a diagram that schematically illustrates an example of a display protocol.

FIG. 5A schematically illustrates the contents of a display protocol. As illustrated in FIG. 5A, this display protocol divides a screen into four small regions Sub1, Sub2, Sub3, and Sub4. An axial tomographic image is reconstructed from CT images and processed according to a window level and a window width as lung field conditions in region Sub1. A coronal tomographic image is reconstructed from CT images and processed according to a window level and a window width as lung field conditions in region Sub2. An axial tomographic image is reconstructed from CT images and processed according to a window level and a window width as mediastinal conditions in region Sub3. A coronal tomographic image is reconstructed from CT images and processed according to a window level and a window width as mediastinal conditions in region Sub4. Note that in actuality, it is necessary for more detailed parameters, such as position of the cross section, to be set as the image processing conditions. However, the image processing conditions are expressed using the terms axial tomographic image, lung field conditions, etc., to simplify the description. FIG. 5B illustrates an example of a display protocol table 23 in which the display protocol of FIG. 5A is registered. As illustrated in FIG. 5B, the display protocol table 23 registers display protocols correlated with display protocol ID's that identify the display protocols, keywords, region ID's that identify regions in the screen, positional information of the regions (the coordinates of the upper left corner, the width (W), and the height (H)), conditions such as the modality of the images to be displayed in the regions (the item IMAGE TO BE OBTAINED), the contents of image processing (the items IMAGE PROCESS 1 and IMAGE PROCESS 2). This display protocol 001, is registered with the keywords "lung" and "nodule", and the attributes of the four regions Sub1, Sub2, Sub3, and Sub4 (positional information, image to be obtained, image process 1, image process 2, . . . ).

Note that it is possible for users such as practice group physicians to perform maintenance, such as registration, change, and deletion, to the display protocols as necessary. The maintenance may be performed by direct settings in the display protocol table 23. However, it is preferable for such maintenance to be performed by settings input through a GUI that enables interactive input or selection of the number of regions that a screen is divided into, the arrangements of the regions, the attributes of the images to be embedded in the regions, image processing conditions, etc.

In the case that the keywords "lung" (keyword K1) and "nodule" (keyword K2) are extracted as keywords by the keyword extracting section 22 as in the example illustrated in FIG. 4, the display protocol determining section 22 searches among keywords registered in the display protocol table 23 exemplified in FIG. 5B, based on the extracted keywords. As a result, protocol "001" is found, and a display protocol DP is specified.

Meanwhile, the image obtaining section 25 first obtains link information IL that enables image data, from which the observation target image 36 attached to the image observation report RPT is generated, to be accessed. Note that as stated in the description of the image observation report database, the link information IL is correlated to the other information in the image observation reports in the image observation report database 8. Therefore, when the practice group workstation 4 obtains an image observation report from the image observation report server 7, the link information IL is obtained with the image observation report RPT. Next, the image obtaining section 25 requests the image information managing server 5 to view an image, based on the link information IL. Thereby, the image obtaining section 25 obtains original data $I_1$ of the image which was the target of observation (hereinafter, observation target image) in the image observation report RPT. In the example illustrated in FIG. 4, the image data $I_1$ is CT image data.

The image processing section 26 administers image processes based on the display protocol DP determined by the display protocol determining section 24 with the image data $I_1$ as input, and outputs processed image data $I_{11}$, $I_{12}$, $I_{13}$, . . . . Note that the image processing section 26 may be provided as separate programs installed for each of various types of processes, such as MPR, MIP, MinIP, volume rendering, and window processes. In the example illustrated in FIG. 4, FIG. 5A, and FIG. 5B, the image processing section 26 reconstructs an axial tomographic image corresponding to the region Sub1 from the CT image using the image data $I_1$ as input data, and generates an image which is processed with the window level and the window depth as lung field conditions. The image processing section 26 also reconstructs coronal tomographic image corresponding to the region Sub2 from the CT image using the image data $I_1$ as input data, and generates an image which is processed with the window level and the window depth as lung field conditions. The image processing section 26 further reconstructs an axial tomographic image corresponding to the region Sub3 from the CT image using the image data $I_1$ as input data, and generates an image which is processed with the window level and the window depth as mediastinal conditions. The image processing section 26 still further reconstructs a coronal tomographic image corresponding to the region Sub4 from the CT image using the image data $I_1$ as input data, and generates an image which is processed with the window level and the window depth as mediastinal conditions.

The display screen generating section 27 generates a display screen SC in which images represented by the processed image data $I_{11}$, $I_{12}$, $I_{13}$, . . . generated by the image processing section 26 are arranged in a display layout based on the display protocol DP determined by the display protocol determining section 24. Thereby, in the example illustrated in FIG. 4, FIG. 5A, and FIG. 5B, the display screen SC, in which images processed by the image processing section 26 are arranged in the regions of the layout illustrated in FIG. 5A, is generated, and displayed on the display of the practice group work station 4.

As described above, the first embodiment presumes a conventional workflow for image diagnosis that includes cooperation between radiologists and practice group physicians. That is, imaging is performed by the modality 1 based on an examination order from a requesting practice group physician. Then, a radiologist in a radiology department performs image observation of image information stored in the image information database 6 at the radiology work station 3, and generates an image observation report RPT. When the generated image observation report RPT is stored in the image observation report database 8, the requesting practice group physician is notified.

Thereafter, the unique viewing functions of medical images of the present invention are realized. Specifically, the requesting practice group physician obtains the image observation report RPT generated by the radiologist from the image observation report database 8 and views the image observation report RPT at the practice group work station 4. When an operation to initiate detailed observation of a desired image is performed, the keyword extracting section 22 extracts keywords K1, K2, . . . that represent information related to anatomical structures and information related to diseases from the image observation report RPT using the keyword table 21. Then, the display protocol determining section 24 automatically selects a display protocol DP that matches the keywords K1, K2, . . . from the display protocol table 23. The image processing section 26 administers image processes on original image data $I_1$ obtained by the image obtaining section 25, based on the display protocol DP, to generate processed images $I_{11}$, $I_{12}$, $I_{13}$, . . . for display Then, the display screen generating section 27 generates a display screen SC, in which the images $I_{11}$, $I_{12}$, $I_{13}$, . . . for display are arranged in a layout based on the display protocol DP. The display screen SC is displayed by the practice group work station 4.

Accordingly, the observation target image and the images for display are generated from the same original data $I_1$. However, the former is employed for image observation by the radiologist, whereas the latter are employed for detailed observation by the practice group physician. In the first embodiment, the images can be those having different image processing conditions and different display conditions.

Thereby, the requesting practice group physician is enabled to observe images which are displayed based on the display protocol DP which is automatically determined based on anatomical structures and diseases which are mentioned in the image observation report RPT generated by the radiologist. Accordingly, the workflow of image diagnosis that includes cooperation between the radiologist and the requesting physician is streamlined without burdening the radiologist or the requesting physician with extraneous work.

Note that in the embodiment described above, the keyword table 21 and the keyword extracting section 22 correspond to the extracting means of the present invention, and the image obtaining section 25, the image processing section 26, and the display screen generating section 27 correspond to the image processing/display control means of the present invention.

In addition, the first embodiment employs the display protocol table 23 illustrated in FIG. 5B, in which display protocols are defined for each modality. Therefore, observation of images in display formats optimal for the modality of the original data $I_1$ for the images for display becomes possible, which contributes to improvements in the efficiency and accuracy of diagnoses.

FIG. 6 is a block diagram that schematically illustrates the structures and the flow of data of a medical image display apparatus according to a second embodiment of the present invention that enables a cooperative viewing function of image observation reports and images which are the subjects of the image observation reports at the practice group work station 4. The second embodiment of the present invention not only displays observation target images correlated to image observation reports, but also displays images having relevancy to the observation target images. Hereinafter, a description will be given mainly of the differences from the first embodiment.

In the second embodiment, the image obtaining section 25 not only obtains original data $I_1$ of observation target images, but also obtains relevant image data $I_2, I_3, \ldots$ of images having a predetermined relevancy to the observation target image from the image information database 6. Examples of specific search conditions are as follows:
(1) Images having the same subject as the subject of the observation target image;
(2) Images that satisfy condition (1), were obtained on the same examination date, and were obtained by a modality different from that of the observation target image; and
(3) Images that satisfy condition (1) and were obtained at an examination date prior to the examination date of the observation target image.

FIG. 7 is a diagram that schematically illustrates the specific contents of the search process. As illustrated in FIG. 7, the image information database 6 stores appended information, such as image ID's, patient ID's, examination dates, modalities, imaging conditions, and file names in the form of a table. In the case that the search condition is (1) described above, the image obtaining section 25 searches in the image information database 6 using a patient ID "12345" correlated with the image observation report RPT as a search key, to obtain image data (image ID="24680") of an image of the same patient as that of the observation target image. Note that image data having the image ID "13579" has an examination ID "1001", which is the same as that correlated with the image observation report RPT. Therefore, it can be understood that the image data having the image ID "13579" is the image data of the observation target image.

The display protocol determining section 24 selects a display protocol DP from the display protocol table 23 based not only on keywords K1, K2, . . . , but also based on information appended to the relevant images obtained by the image obtaining section 25.

FIG. 8A is a diagram that illustrates an example of the contents a display protocol that simultaneously displays an image which is a target of image observation and a relevant image. The display protocol of FIG. 8A differs from the display protocol illustrated in FIG. 5A in that the modalities of the images to be displayed in regions Sub3 and Sub4 are HRCT (High Resolution Computed Tomography). That is, the display protocol not only displays observation target images, but also displays relevant images relevant thereto. FIG. 8B illustrates an example of a display protocol table 23 in which the display protocol of FIG. 8A is registered. As illustrated in FIG. 8B, "Input" that represents observation target images is listed in the column "Image to be Obtained" for regions Sub1 and Sub2, to differentiate the observation target images and relevant images. "Same Day (the examination date is the same as that of the observation target image)" is listed in the column "Image to be Obtained" for regions Sub3 and Sub4, and "HRCT" is listed as the modalities of the relevant images. In this example, the display protocol determining section 24 employs keyword K1 ("lung") and keyword K2 ("nodule") extracted by the keyword extracting section 22, compares the information appended to the relevant images obtained by the image obtaining section 25 against the values of the images to be obtained in the display protocol table 23, and selects a display protocol that satisfies both the conditions of the keywords and of the images to be obtained. For example, a relevant image having the image ID "24680" of FIG. 7 has the same examination date as the observation target image and a modality of HRCT, and therefore satisfies the condition regarding the image to be obtained. Here, in the case that the image information database has stored therein images of the same patient and obtained on the same examination date as the observation target image but with a modality other than HRCT, such display protocols are not selected. Note that in the case that no display protocols that satisfy all of the conditions of the image to be obtained are registered in the display protocol table 23, display protocols having the highest degrees of priority from among display protocols that satisfy the keyword conditions may be selected. In addition, in the case that a great number of relevant images are present, and display protocols having different conditions regarding images to be obtained are present, there is a possibility that there are a plurality of display protocols that satisfy both the keyword conditions and the conditions regarding images to be obtained. In such cases as well, display protocols having the highest degrees of priority may be selected, or display protocols that satisfy both conditions may be displayed as a list.

Figure 9E:
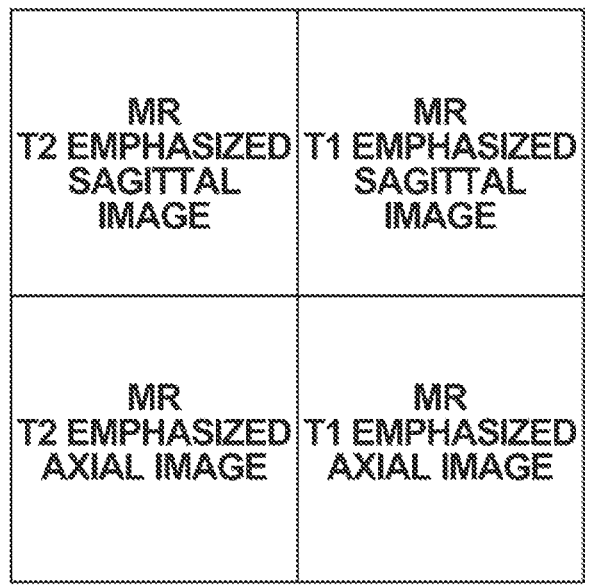
FIG. 9E is a fifth diagram that schematically illustrates another example of a display protocol that simultaneously displays an image which is a target of image observation and a relevant image.

FIG. 9A through FIG. 9E illustrate examples of display protocols that display observation target images and relevant images simultaneously. FIG. 9A illustrates a display protocol for a case in which the disease to be observed is diffuse lung disease. FIG. 9B illustrates a display protocol for a case in which the disease to be observed is a lung nodule, and both CR images and CT images are displayed simultaneously.

FIG. 9C illustrates a display protocol for a case in which the disease to be observed is a lung nodule, and a present CT image and a past CT image are displayed simultaneously. FIG. 9D illustrates a display protocol for a case in which the disease to be observed is cerebral Alzheimer's disease. FIG. 9E illustrates a display protocol suited for a case in which the disease to be observed is an intervertebral disc hernia. In these cases as well, judgments regarding the conditions of images to be obtained in the display protocol table 23 are rendered by employing the appended information in the image information database 6 illustrated in FIG. 7, such as examination dates, the modalities, and imaging conditions.

The image processing section 26 administers image processes according to the definitions of the display protocol DP determined by the display protocol determining section 24 on the image data $I_1$ of the observation target image obtained by the image obtaining section 25. In addition, the image processing section 26 administers image processes according to the definitions of the display protocol DP on image data $I_2$, which is to be displayed according to the display protocol DP from among image data $I_2$ and $I_3$ of relevant images obtained by the image obtaining section 25, to generate processed images $I_{11}, I_{12}, \ldots, I_{21}, I_{22}, \ldots$.

As described above, in the second embodiment of the present invention, the image obtaining section 25 (corresponding also to the relevant image search means of the present invention) searches in the image information database 6 to obtain not only the original data $I_1$ of the observation target image, but also image data $I_2$ and $I_3$ if relevant images which are relevant to the original data $I_1$. The display protocol determining section 24 selects a display protocol DP that satisfies both conditions regarding the keywords K1 and K2 related to anatomical structures and diseases and conditions regarding the attributes of the related images, based on the display protocol table 23 that defines formats for simultaneously displaying the observation target image and the relevant images. Therefore, comparative observation with optimal relevant medical images according to anatomical structures and diseases becomes possible, which contributes to improvements in the efficiency and accuracy of diagnosis.

Note that in the second embodiment, the display protocol determining section 24 selects relevant images to be displayed and determines the display protocol DP after the image obtaining section 25 obtains the relevant images. Alternatively, the display protocol determining section 24 may preliminarily determine a display protocol DP based only on keywords K1, K2, . . . first, then the image obtaining section 25 may obtain relevant images that satisfy the conditions defined in the preliminarily determined display protocol by searching in the image information database 26. Specifically, in the case of the display protocol illustrated in FIG. 8A and FIG. 8B, the image obtaining section 25 would not search for all images of the patient as that of the observation target image, but only for images of the same patient, having the same examination date and a HRCT as the modality.

As a further modification to the second embodiment, a display protocol DP may be defined such that images having the same medical opinions as those described in image observation reports RPT regarding observation target images are displayed as relevant images. In this case, the image obtaining section 25 obtains image data of images having the same medical opinions as those of the observation target images. Specifically, with respect to the display protocol DP, in the case of the display protocol tables 23 illustrated in FIG. 5B and FIG. 8B, "Same Opinion CT" may be registered in the "Image to be Obtained" column. Meanwhile, with respect to the image obtaining section 25, if medical opinions related to images are stored in the image information database 3, images having the same opinions as those of the observation target images, images having opinions related to a nodule in the upper lobe of the left lung or images having opinions related to 3 cm diameter nodules in the lungs may be obtained by searching in the image information database 6 with respect to the example of FIG. 3A, for example. Alternatively, the image obtaining section 25 may search for image observation reports that include the same opinions as those of the observation target images within the image observation report database 8, and may obtain image data of images correlated to the found image observation reports from the image information database 6.

In the embodiments described above, the display protocols include both image processing conditions and display conditions. Alternatively, display protocols may define only image processing conditions, as in a third embodiment of the present invention to be described below.

Figure 12:
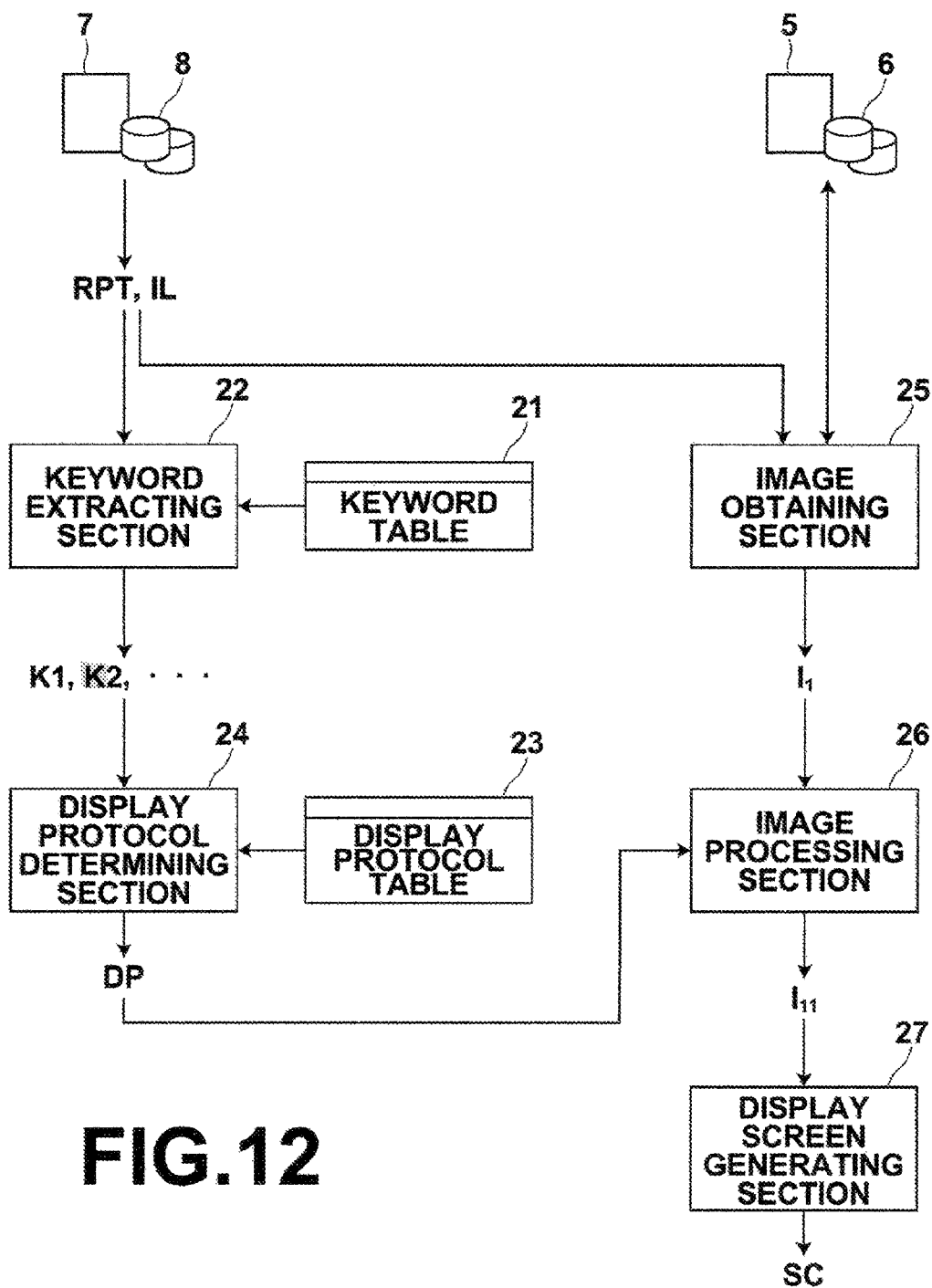
FIG. 12 is a block diagram that schematically illustrates the structures and the flow of processes that realize the medical image display function of a third embodiment of the present invention.

FIG. 12 is a block diagram that schematically illustrates the structures and the flow of data of a medical image display apparatus according to the third embodiment of the present invention which is incorporated into the practice group work station 4. The medical image display apparatus of the third embodiment differs from that of the first embodiment in that the display screen generating section 27 does not refer to a display protocol DP determined by the display protocol determining section 24, but generates a display screen SC, in which an image represented by processed image data $I_{11}$ is arranged in a predetermined display layout.

FIG. 13 is a diagram that illustrates examples of display protocols that only define image processing conditions registered in a display protocol table 23. As illustrated in FIG. 13, information that identify keywords, types of images to be generated, masks (targets of automatic discriminating processes), display/non display of the targets of the masks, and color templates are registered with respect to display protocol ID's that identify display protocols. In the case the keyword "Liver" is extracted, and "VR (Volume Rendered) Image" is selected as the image to be generated, display protocol "101" defines image processing conditions such that the "Liver" is automatically discriminated and displayed employing color template "Color 01". In the case the keywords "Liver" and "Spleen" are extracted, and "VR (Volume Rendered) Image" is selected as the image to be generated, display protocol "102" defines image processing conditions such that the "Liver" and "spleen" are automatically discriminated and displayed employing color template "Color 02". In the case the keyword "Blood Vessel" is extracted, and "VR (Volume Rendered) Image" is selected as the image to be generated, display protocol "103" defines image processing conditions such that "Bone" is automatically discriminated and not displayed (by administering a bone removing process) and such that color template "Color 11" is employed. In the case the keyword "Heart" is extracted, and "VR (Volume Rendered) Image" is selected as the image to be generated, display protocol "104" defines image processing conditions such that the "Heart" and "Coronary Arteries" are automatically discriminated and displayed employing color template "Color 21". In the case the keywords "Brain" and "Blood Vessel" are extracted, and "MIP Image" is selected as the image to be generated, display protocol "105" defines image processing conditions such that color template "Monochrome 01" is employed. In the case the keywords "Brain" and "Blood Vessel" are extracted, and "VR (Volume Rendered) Image" is selected as the image to be generated, display protocol "106" defines image processing conditions such that the "Blood Vessel" is automatically discriminated and displayed employing color template "Color 31". Note that the display protocol table of the third embodiment may alternatively be the display protocol table of FIG. 5B from which the columns "Region ID" and "Positional Information" are deleted.

Figure 14A:
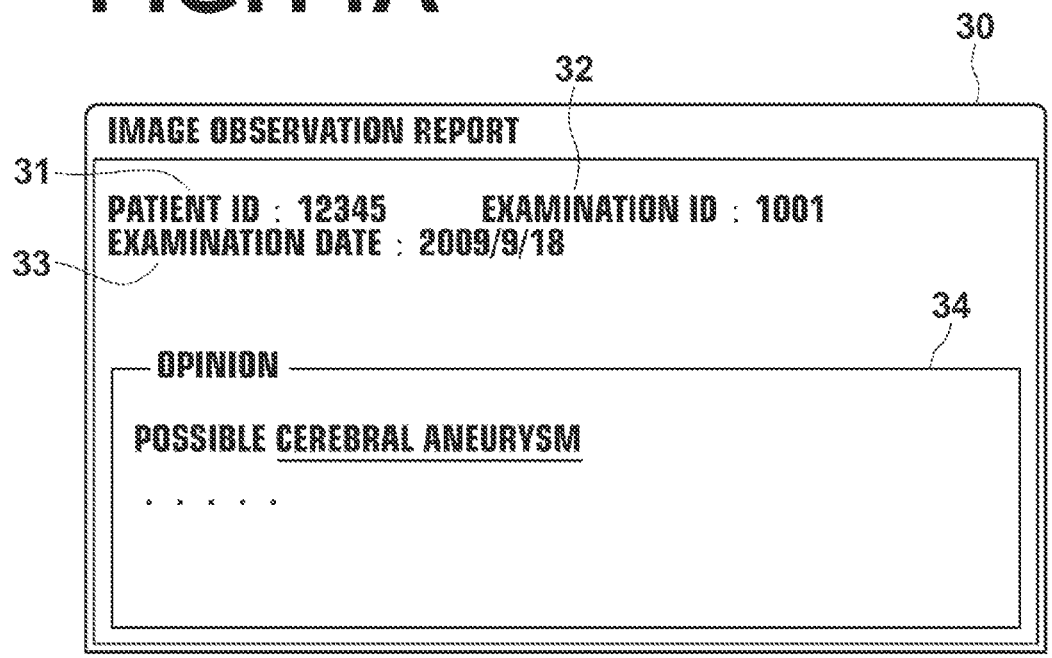
FIG. 14A is a diagram that schematically illustrates an example of a display screen of an image observation report in the third embodiment of the present invention.
Figure 14B:
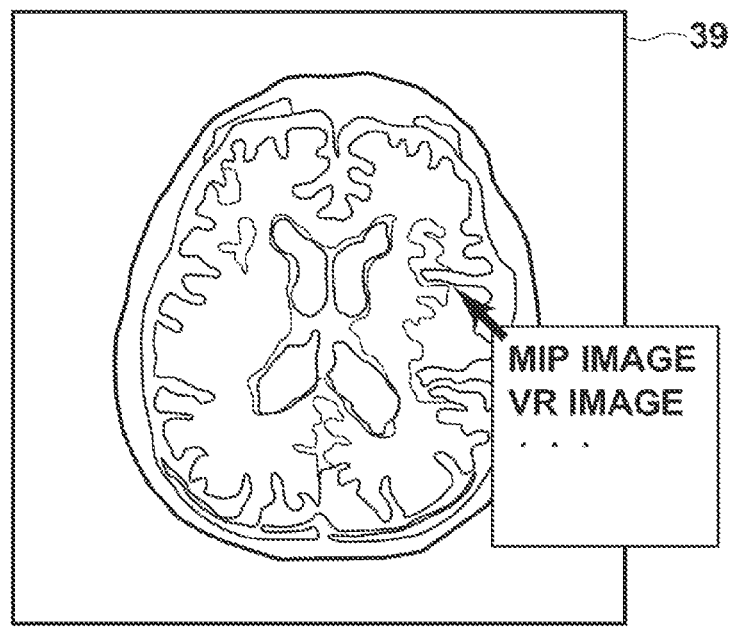
FIG. 14B is a diagram that schematically illustrates an example of a pop up screen that displays an image which is a target for image observation in the third embodiment of the present invention.

FIG. 14A is a diagram that illustrates a specific example of a case in which a software program that realizes the cooperative viewing functions of image observation reports and images that the image observation reports are related to is booted up in the third embodiment of the present invention. As illustrated in FIG. 14A, a display screen 30 of an image observation report is the display screen illustrated in FIG. 3B from which the region 35 for displaying the thumbnail image 35 of the observation target image is removed. When a user clicks the link "Possible Cerebral Aneurysm" set in region 34 in which the medical opinion is displayed, a pop up screen 39 that includes an observation target image as illustrated in FIG. 14B. If the user right clicks the observation target image, a menu for selecting an image to be displayed is displayed. If "MIP Image" is selected, for example, the program is booted up, the keyword extracting section 22 refers to the keyword table 21, and extracts the keywords "Brain" and "Blood Vessel". Next, the display protocol determining section 24 refers to the display protocol table 23 based on the extracted keywords "Brain" and "Blood Vessel" and also the type of image "MIP Image" which was selected, and obtains the display protocol "105". The image processing section 26 generates processed image data $I_{11}$ by administering an MIP process on original data $I_1$ of the observation target image obtained by the image obtaining section 25 employing the color template "Monochrome 01", based on the display protocol "105" determined by the display protocol determining section 24 and the type of image "MIP Image" selected in the pop up screen 39 of FIG. 14B. The display screen generating section 27 updates the image displayed in the pop up window 39 to the processed image $I_{11}$.

Figure 15:
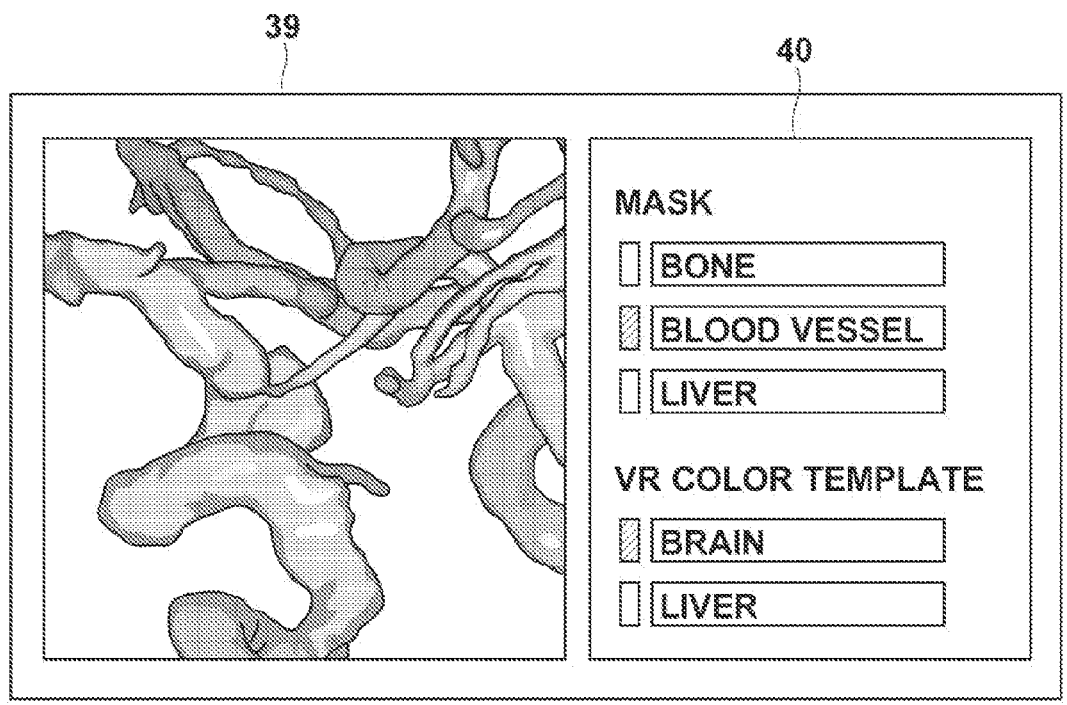
FIG. 15 is a diagram that illustrates an example of a pop up screen that displays image processing conditions in a modification to the third embodiment of the present invention.

In addition, a region 40 for displaying the contents of the image processing conditions applied by the image processing section 26, that is, the contents of the image processing conditions determined by the display protocol determining section 24 may be provided in the pop up window 39 as illustrated in FIG. 15. The image of FIG. 15 is that which is generated based on display protocol "106". In FIG. 15, the region 40 indicates that masks that display blood vessels are set to be displayed and that a color template for volume rendering of the brain is selected. Note that if anatomical structures specified by masks are set to be not displayed, an "X" may be displayed in a rectangular radio button in the region 40. Thereby, users are enabled to easily understand what image processing conditions are selected for the image being presently displayed. Further, a configuration may be adopted in which operations to change the selected radio buttons (the hatched rectangle) are received, and the image processing section 26 regenerates an image based on the changed image processing conditions. In this case, the display screen generating section 27 may update the displayed image to the regenerated image.

Further, in the case that descriptions related to diseases such as nodules are present in image observation reports, positional information of the diseases may be recorded correlated with the image observation reports, and the positional information may be employed as one of the image processing conditions. For example, the image processing section 26 may administer image processes such that the positions of diseases are the centers of the fields of view of volume rendered images and the like.

Note that the above embodiment was described as a case in which the image processing section generates only one image, for the sake of convenience. Alternatively, the display protocol table 23 may have display protocols which are defined to generate a plurality of images, and a plurality of images may be generated based thereon. For example, a definition that generates a volume rendered image from which bones are removed using a color template for blood vessels as in protocol "103" of FIG. 13 and a definition that generates an MIP image from which bones are removed using a monochrome template for blood vessels may be correlated to the keywords "blood vessel" and "disease".

As an alternative to the third embodiment described above, display protocols may define only display conditions, as in a fourth embodiment of the present invention to be described below.

FIG. 16 is a block diagram that schematically illustrates the structures and the flow of data of a medical image display apparatus according to the fourth embodiment of the present invention which is incorporated into the practice group work station 4. As illustrated in FIG. 16, the image obtaining section 25 refers to a display protocol DP determined by the display protocol determining section 24, and obtains image data $I_{11}, I_{12}, I_{13}, \ldots$ of images, which have been processed as images for display according to the definitions in the display protocol DP, from the image information database 5. The display screen generating section 27 generates a display screen SC, in which images are arranged in a display layout based on the display protocol DP determined by the display protocol determining section 24.

In the embodiments described above, the display protocol table 23 was provided with display protocols common to all users. Alternatively, display protocols may be defined for each user or for each group (a neurosurgery group, for example) constituted by a plurality of users. Specifically, different display protocol tables may be provided for each user or for each group. Alternatively, columns related to user ID's or group ID's may be added to the display protocol table, ID's used to log in to the practice group medical image work station 4 may be referred to, and access may be enabled only to display protocols defined with the user or the group.

Further, display protocols may be defined for intended uses, such as image observation, referral, and conferences. In this case, display protocols corresponding to an intended use input by a user may be selected.

Alternatively, display protocols may be defined for each type of display device of the work stations. In this case, the display protocol determining section 24 may obtain information related to the display device from the operating system or the like, and a display protocol may be selected further based on the type of display device. Here, specific examples of types of display devices include: the number of monitors (single screen, double screen, etc.); the size of the monitor; whether the display device is capable of stereoscopic display; and whether the display device is a desktop terminal or a mobile terminal.

As a further alternative, display protocols may be defined for each type of input device of the work stations. In this case, the display protocol determining section 24 may obtain information related to the input device from the operating system or the like, and a display protocol may be selected further based on the type of input device. Here, specific examples of types of input devices include: the type of the input device itself, such as a mouse and a touch panel; and whether the input device is equipped with various operational functions, such as right clicking and wheel scrolling.

Further, display protocols may be defined for each installation location of the work stations. In this case, the display protocol determining section 24 may obtain information related to the installation location from the network address of the work station, and a display protocol may be selected further based on the installation location. Here, specific examples of installation locations include: specific rooms within a hospital, such as conference rooms, operating rooms, image observation rooms, and examining rooms; information regarding the sizes of hospitals, such as general hospitals, university hospitals, and private practices; remote locations; and information that identifies individual hospitals.

Still further, display protocols may be defined for display timings. In this case, the display protocol determining section 24 may obtain information related to the display timing, and a display protocol may be selected further based on the display timing. Here, specific examples of display timings include: prior to surgery; during surgery; and following surgery. Specific examples of methods for obtaining information related to the display timing include: receiving input from users; obtaining surgical histories of patients from information appended to input images or from a database in which patient information is registered; and obtaining text that represent display timings from image observation reports.

FIG. 11A and FIG. 11B illustrate two different display protocols for a liver tumor. In cases such as this, in which a plurality of display protocols may be considered for the same disease in the same organ, display protocols may be selectively utilized according to the user, the group, the intended use, the display device, the input device, the installation location, and the display timing.

Alternatively, display protocols may be defined for each attribute of the original data $I_1$ obtained based on the link information IL. In this case, the display protocol determining section 24 may obtain information related to the attributes of the original data $I_1$, and a display protocol may be selected based further on the attributes of the original data $I_1$. For example in the case that the original data $I_1$ are temporal series data, image processing conditions may be defined for image data of each temporal phase, and display conditions, such as sequentially displaying processed images for each temporal phase in temporal order at predetermined temporal intervals, may be defined in the display protocol table 23. Thereby, image for display may be reproduced as videos.

As a further alternative, a region for receiving input of information that enables specification of display protocols may be provided when generating image observation reports. The input information may be employed in the series of processes for determining a display protocol. Specifically, keywords may be input into this region, and the display protocol determining section 24 may determined a display protocol employing the input keywords. In this case, the input keywords may be prioritized, or employed as additional information to keywords extracted from the contents of the medical opinions in the image observation reports. Alternatively, display protocol ID's such as those illustrated in FIG. 5B may be input into this region, and the display protocol determining section 24 may determine display protocols based on the input display protocol ID's.

Various changes and modifications to the system configuration, the process flow, and the module configuration of the above embodiments are possible as long as they do not stray from the concept of the present invention. Such changes and modifications are included in the technical scope of the present invention.

Figure 10:
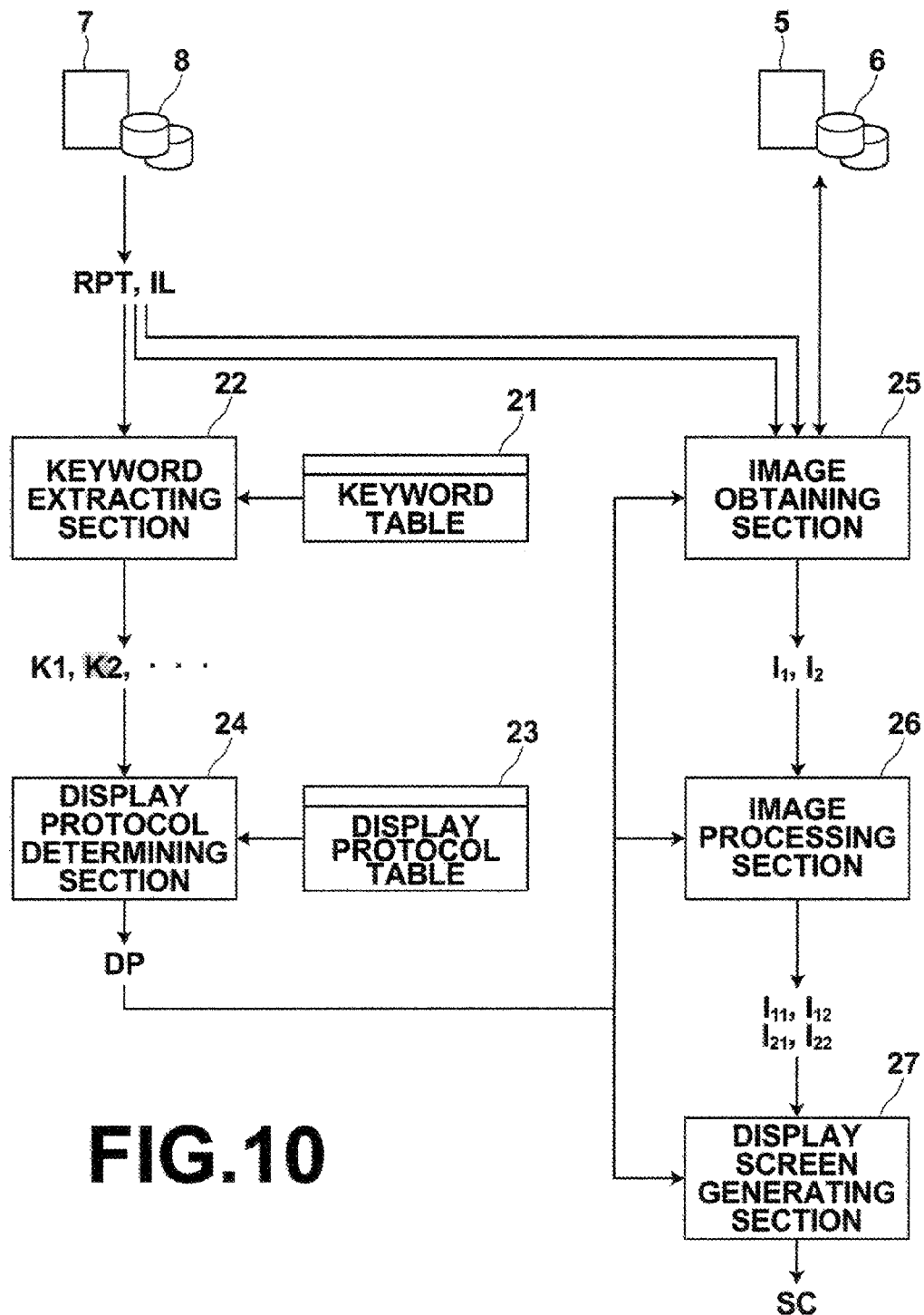
FIG. 10 is a block diagram that schematically illustrates the structures and the flow of processes that realize the medical image display function of a modification to the second embodiment of the present invention.

For example, the embodiments have been described as cases in which the processes illustrated in FIGS. 2, 6, and 10 were performed by a single practice group work station 4. However, a configuration may be adopted in which the processes are divided among a plurality of work stations and executed cooperatively.

The above embodiments are merely illustrative, and the descriptions thereof are not to be utilized to interpret the technical scope of the present invention in a limiting manner.

The invention claimed is:

1. A medical image display apparatus, comprising:
a display protocol storing section, for storing display protocols, which are defined by image processing conditions for generating medical images for display from input medical image data and/or display conditions of the medical images for display being correlated with information regarding anatomical structures and/or information regarding diseases;
an extracting section, for extracting information regarding anatomical structures and/or information regarding diseases from within medical opinions regarding observation target images included in image observation report information regarding the input medical image data;
a display protocol determining section, for determining display protocols for the medical images for display by selecting display protocols from among those stored in the display protocol storing section, based on the extracted information regarding anatomical structures and/or information regarding diseases;
an image processing/display control section, for generating the medical images for display from the input medical image data and controlling display of the medical images for display, based on the determined display protocols; and
an image observation report viewing section, for viewing the image observation report; wherein:
when the input of an operation to display the medical images for display is received while viewing the image observation report, the extracting section, the display protocol determining section, and the image processing/display control section are booted up.

2. A medical image display apparatus as defined in claim 1, wherein:
the display protocols are further correlated with the modalities of the input medical image data; and
the display protocol determining section determines the display protocol for the input medical image data based further on the modality of the input medical image data.

3. A medical image display apparatus as defined in claim 1, wherein:
the display protocols further define image processing conditions for generating relevant medical images for display from relevant medical image data, which have the same subject as a subject of the input medical image data, and display conditions for the relevant medical images for display;
the medical image display apparatus further comprises:
a medical image database having stored therein medical image data and subject information regarding the medical image data; and
a relevant image search section, for performing searches for the relevant medical image data in the medical image database; and wherein
the display protocol determining section determines the display protocols based on a modality and/or an examination date of the input medical image and the searched relevant medical image data; and
the image processing/display control section obtains the relevant medical image data from the medical image database, and displays the medical images for display and the relevant medical images for display, based on the determined display protocols.

4. A medical image display apparatus as defined in claim 1, wherein:
the display protocols further define image processing conditions for generating relevant medical images for display from relevant medical image data, which have the same subject as a subject of the input medical image data, and display conditions for the relevant medical images for display;
the medical image display apparatus further comprises:
a medical image database having stored therein medical image data and subject information regarding the medical image data; and wherein:
the image processing/display control section obtains relevant medical image data, which is imaged by the same modality as the modality of the input medical image and/or which is imaged at a same examination date as an examination date of the input medical image, from the medical image database, and displays the medical images for display and the relevant medical images for display, based on the determined display protocols.

5. A medical image display apparatus as defined in claim 1, further comprising:
a display protocol editing section, for editing display protocols which are stored in the display protocol storing section and/or for adding new display protocols.

6. A medical image display method, comprising the steps of:
extracting, in an extracting section, information regarding anatomical structures and/or information regarding diseases from within medical opinions regarding observation target images included in image observation report information regarding input medical image data;
determining display protocols, in a display protocol determining section, for the medical images for display by selecting display protocols from among display protocols, which are defined by image processing conditions for generating medical images for display from input medical image data and display conditions of the medical images for display being correlated with information regarding anatomical structures and/or information regarding diseases, based on the extracted information regarding anatomical structures and/or information regarding diseases; and
generating the medical images, in an image processing/display control section, for display from the input medical image data and/or controlling display of the medical images for display, based on the determined display protocols;
viewing the image observation report; wherein:
when the input of an operation to display the medical images for display is received while viewing the image observation report, booting up the extracting section, the display protocol determining section and the image processing/display control section.

7. A non-transitory computer readable recording medium having a medical image display program stored therein, the medical image display program causing a computer to execute the procedures of:
extracting information, in an extracting section, regarding anatomical structures and/or information regarding diseases from within medical opinions regarding observation target images included in image observation report information regarding input medical image data;
determining display protocols, in a display protocol storing section, for the medical images for display by selecting display protocols from among display protocols, which are defined by image processing conditions for generating medical images for display from input medical image data and display conditions of the medical images for display being correlated with information regarding anatomical structures and/or information regarding diseases, based on the extracted information regarding anatomical structures and/or information regarding diseases; and
generating the medical images, in an image processing/display section, for display from the input medical image data and/or controlling display of the medical images for display, based on the determined display protocols;
an image observation report, viewing section, for viewing the image observation report; wherein:
when the input of an operation to display the medical images for display is received while viewing the image observation report, booting up the extracting section, the display protocol determining section and the age processing/display control section.

8. A medical image display apparatus as defined in claim 1, wherein:
the image processing conditions include one or more types of the medical images for display; and
the medical image display apparatus further comprises:
a selection input receiving section, for displaying a plurality of types of the medical images for display after the input of the operation to display the medical images for display, in case that the plurality of types of the medical images for display is determined based on the extracted information regarding anatomical structures and/or information regarding diseases by the display protocol determining section, and receiving a selection input representing one or more types of the medical images for display that is selected among the displayed types of the medical images for display; and
the image processing/display control section generates the selected one or more types of medical images for display.

9. A medical image display apparatus as defined in claim 1, wherein:
the input medical image data is three dimensional image data;
the observation target images is axial tomographic image;
the image processing conditions include one or more types of the medical images for display;
the types of the medical images for display is at least one of MPR, MIP, MinIP, and volume rendered images.

10. A medical image display apparatus as defined in claim 9, further comprising:
a user information obtaining section, for obtaining user information that identifies users of the medical image display apparatus;
the display protocols being further correlated with the user information or group information that identifies groups constituted by a plurality of users;
the display protocol determining section determining the display protocols based further on the user information or the group information; and
the image observation report is attached to other user information which represent that the image observation report is generated by a user different from the users of the medical image display apparatus.

* * * * *